United States Patent [19]
Vahaviolos

[11] 3,986,391
[45] Oct. 19, 1976

[54] METHOD AND APPARATUS FOR THE REAL-TIME MONITORING OF A CONTINUOUS WELD USING STRESS-WAVE EMISSION TECHNIQUES

[75] Inventor: Sotirios John Vahaviolos, East Windsor Township, Mercer County, N.J.

[73] Assignee: Western Electric Company, Inc., New York, N.Y.

[22] Filed: Sept. 22, 1975

[21] Appl. No.: 615,735

[52] U.S. Cl. .......................... 73/88 R; 219/121 LM
[51] Int. Cl.² ........................................ G01N 29/04
[58] Field of Search ............. 73/88 R, 69, 552, 555, 73/88.3; 219/121 R, 131 R, 121 LM

[56] References Cited
UNITED STATES PATENTS

| | | | |
|---|---|---|---|
| 3,299,250 | 1/1967 | Vilkas | 219/131 R |
| 3,865,201 | 2/1975 | Haden | 73/88 R UX |

OTHER PUBLICATIONS

Herzog, R. E. Forecasting Failures with Acoustic Emission, From Machine Design, June 14, 1973, vol. 45, pp. 132–137.

*Primary Examiner*—Jerry W. Myracle
*Attorney, Agent, or Firm*—E. W. Pfeifle; D. J. Kirk

[57] ABSTRACT

Continuous welds are monitored by detecting and processing stress-wave signals emitted from the moving weld area to provide an indication of both the weld energy supplied to the weld area by the welding apparatus, and the development of microcracks in the cooling weld area. According to the present invention, the detected stress-wave signals emitted from the weld area are amplified and filtered to provide excellent signal-to-noise ratios and then applied to either one, or both, of (a) an RMS voltmeter, and (b) a spectrum analyzer to provide an indication of the weld energy supplied to the weld area and the development of cracks in the cooling weld area.

14 Claims, 5 Drawing Figures

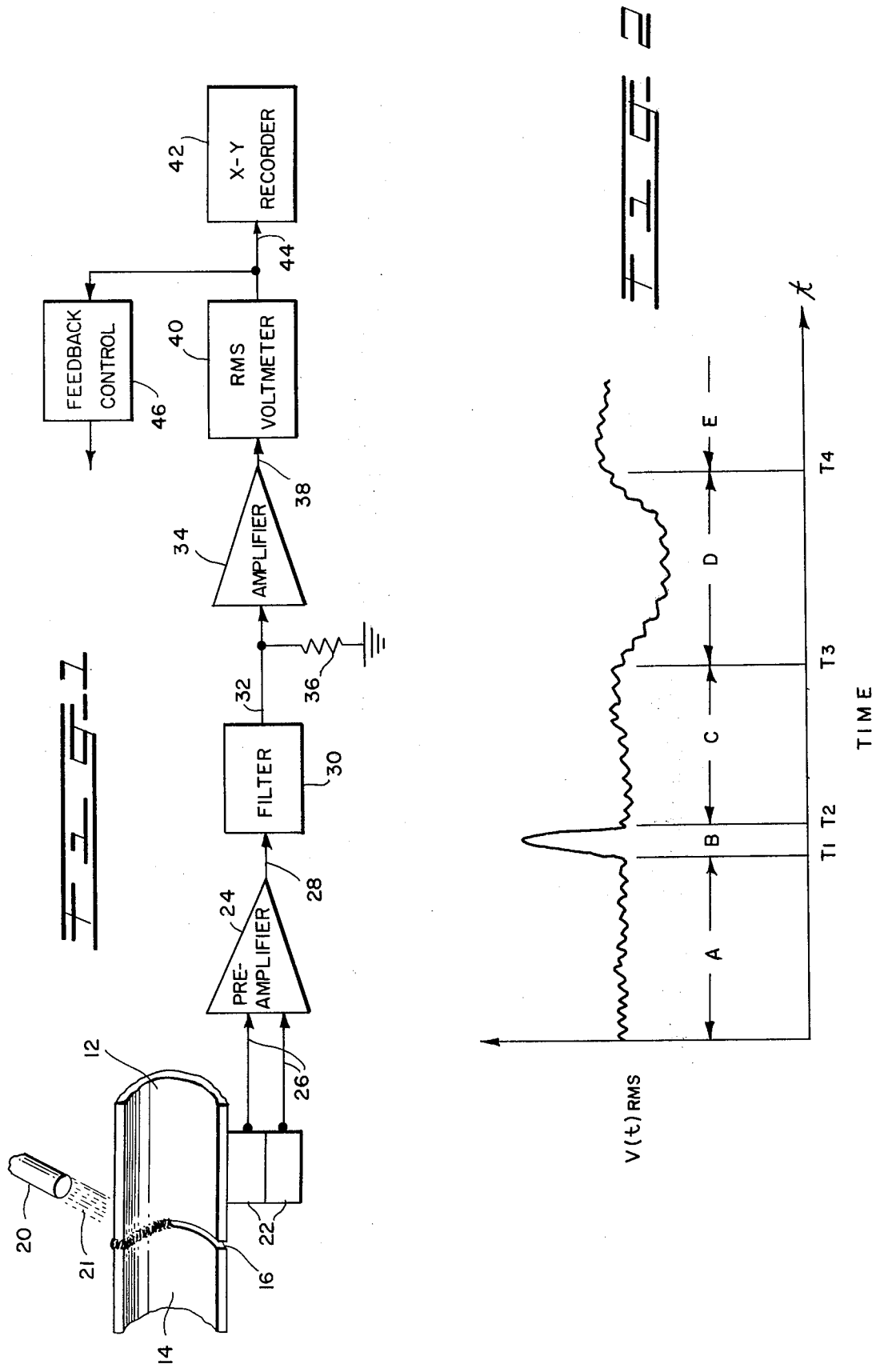

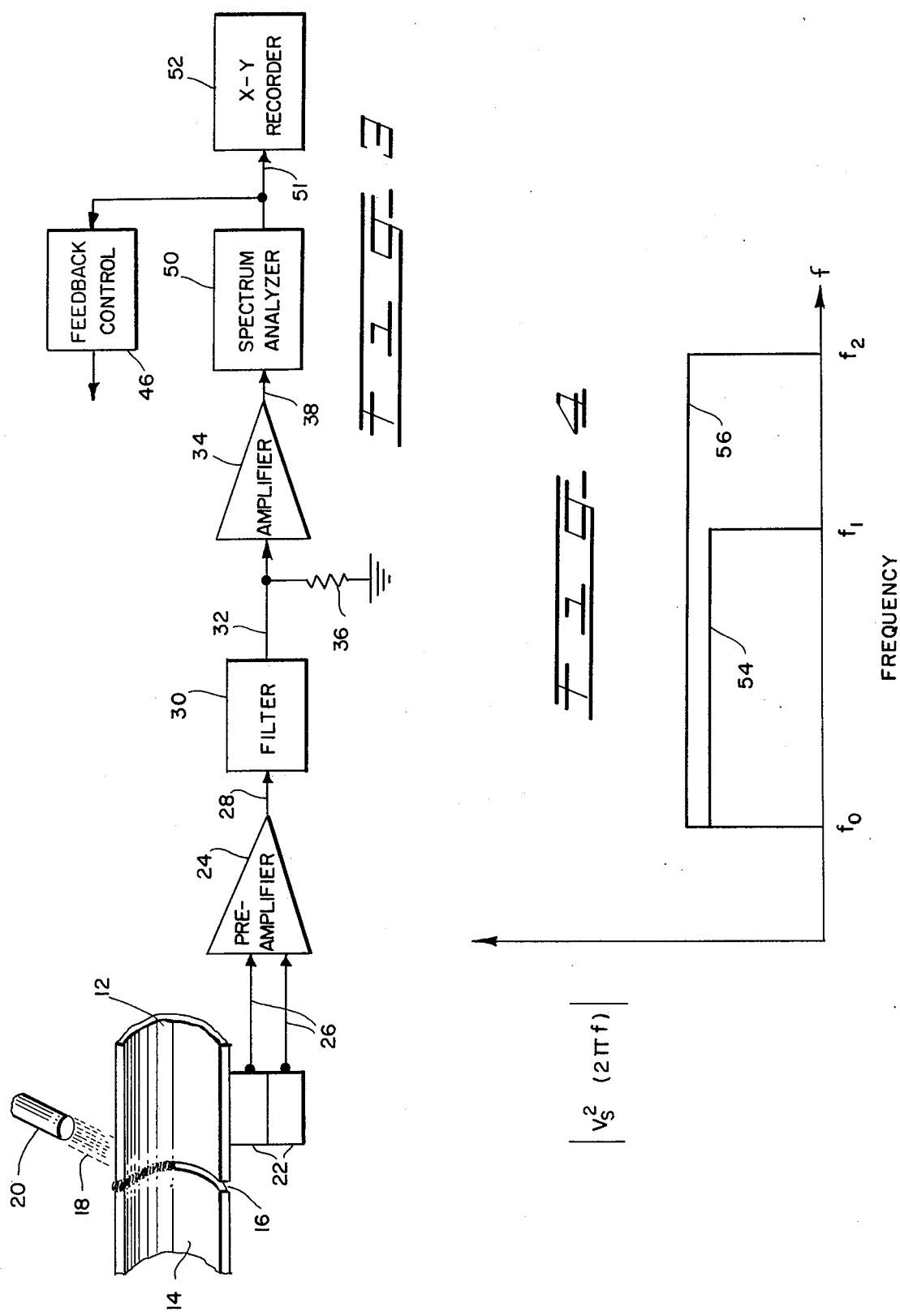

3,986,391

METHOD AND APPARATUS FOR THE REAL-TIME MONITORING OF A CONTINUOUS WELD USING STRESS-WAVE EMISSION TECHNIQUES

BACKGROUND OF THE INVENTION

1. Field of the Invention

The present invention relates to method and apparatus for the real-time monitoring of a continuous weld using stress-wave emission techniques and, more particularly, to method and apparatus which monitors the harmonic content and the energy level of the stress waves emitted from a continuous weld to determine the quality of the weld.

2. Description of the Prior Art

Continuous welds, which can be defined as welds formed along particular paths or lines as opposed to spot welds, have in the past been evaluated after the weld was completed by, for example, scanning the weld area with systems using ultrasonic or X-ray techniques to detect flaws in the weld. The ability to evaluate a continuous weld using real-time, non-destructive methods has, therefore, always been of interest to industry.

A method for monitoring a spot-welding operation is disclosed in U.S. Pat. No. 3,726,130, issued to R. P. Hurlebaus on Apr. 10, 1973. There, ultrasonic shear wave-pulse signals are transmitted into the two pieces to be welded from a transducer positioned opposite the welding electrode while the welding operation is being performed. These signals are reflected from the area between the melting metal and the solid metal to provide real-time data for detecting the degree of penetration of a weld.

Another method for monitoring a spot-welding operation is disclosed in an article entitled "Forecasting Failures with Acoustic Emission," by R. E. Herzog published in *Machine Design*, June 14, 1973, at pages 132 to 137. There it is stated that one of the more successful uses of acoustic emissions is in inspecting welds as they are being made by detecting and correlating signals emitted during the liquid-to-solid phase transformation of a weld area to indicate good or bad welds. The Herzog article further specifies that complex stress waves occur in both the weld cycle and post-weld cooling period, but only emissions during the post-weld cooling period are used for finding defects, such as cracks, as they occur in the weld area, and that emissions during the weld cycle are ignored.

It is also known to detect and measure the stress waves emitted from a spot-weld area during $n$ time intervals of the weld cycle, where $n \geq 4$, each interval corresponding to a different aspect occurring in the weld area during the weld cycle such as, for example, the initiation of heating, the solid-to-liquid phase transformation, the liquid-to-solid phase transformation, and post-weld cracking. The measurements obtained for the intervals are compared with predetermined acceptable ranges for measurements selected from corresponding ones of the intervals and the ratio between measurements of two or more of the intervals thereof to determine the quality and the extent of a spot weld.

The problem still remains of providing method and apparatus which will evaluate a continuous weld as the weld is being made.

BRIEF SUMMARY OF THE INVENTION

The present invention relates to method and apparatus for the real-time monitoring of a continuous weld using stress wave emission techniques and, more particularly, to method and apparatus for monitoring the harmonic content and the energy level of the stress waves emitted from a continuous weld to determine the quality thereof.

Other and further aspects of the present invention will become apparent during the course of the following description and by reference to the accompanying drawings.

BRIEF DESCRIPTION OF THE DRAWINGS

Referring now to the drawings, in which like numerals represent like parts in the several views:

FIG. 1 is a simplified block diagram of a continuous weld-evaluating system according to a preferred embodiment of the present invention;

FIG. 2 depicts a typical output waveform of the weld-evaluating system of FIG. 1 as reproduced on the X–Y recorder thereof;

FIG. 3 is a simplified block diagram of a continuous weld-evaluating system according to another preferred embodiment of the present invention;

FIG. 4 depicts a typical output waveform of the weld-evaluating system of FIG. 3 as reproduced on the X–Y recorder thereof.

DETAILED DESCRIPTION

Figure 5:
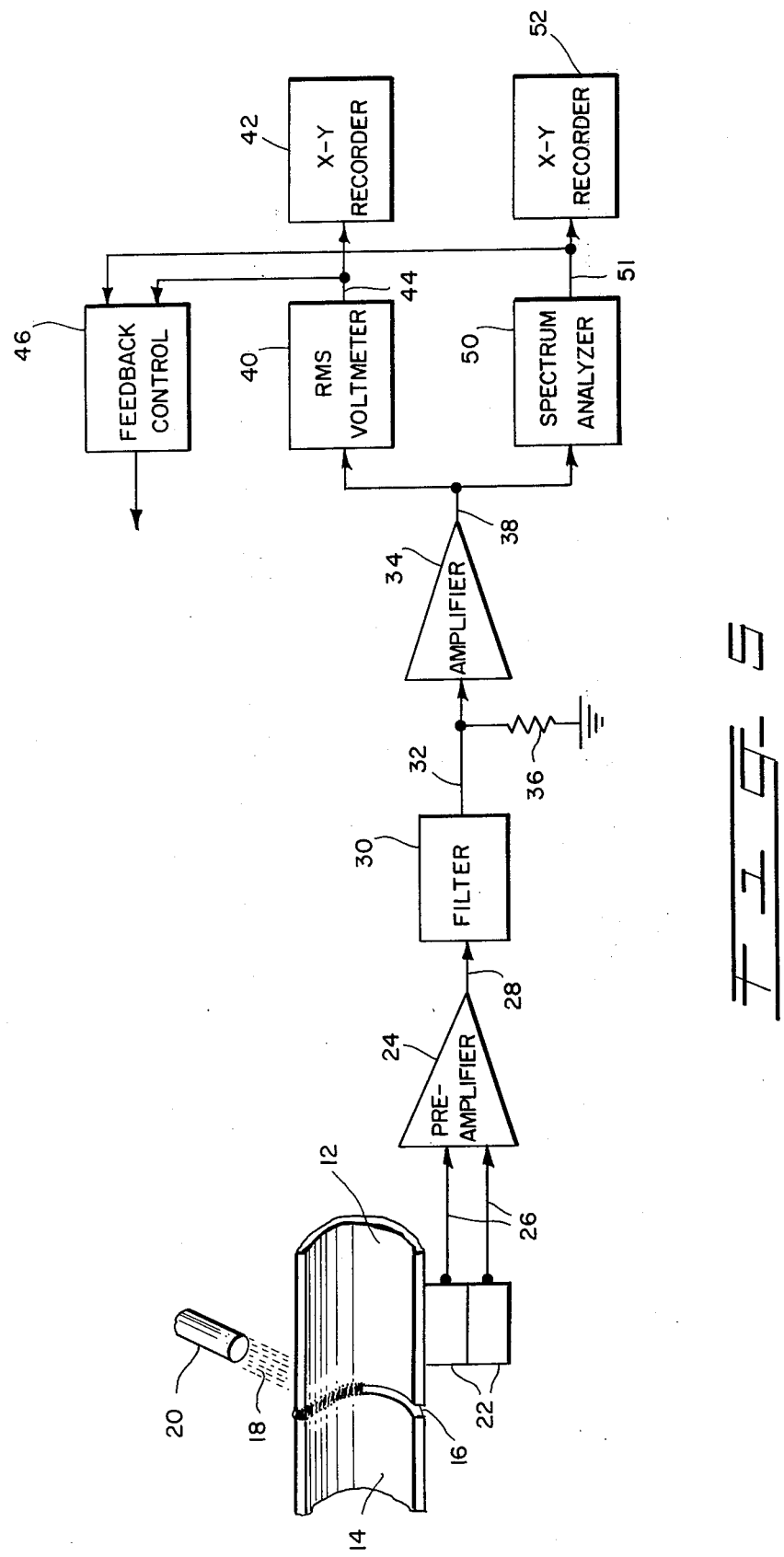
FIG. 5 is a simplified block diagram of a continuous weld-evaluating system according to still another preferred embodiment of the present invention.

The welding process occurs by engaging the articles to be welded in the desired position, melting the articles at their common interface, causing material combination, and permitting the molten volume to solidify. The required interfacial heat can be supplied in a number of different ways, one of which is by laser welding where a beam of radiation is projected at the articles in the area of the desired weld. The present invention is described primarily with relation to a laser welding device, however, it will be understood that such a description is exemplary only and is for purposes of exposition and not for purposes of limitation. It will be readily appreciated that the inventive concept is equally applicable for use with any other continuous welding apparatus, such as, for example, an electron beam welder.

In applying stress-wave emission techniques to the monitoring of continuous welds it must be realized that the continuous weld nugget area is moving and is continually emitting mechanical stress waves from (a) the solid-to-liquid phase transformation at the leading edge of the weld nugget, (b) the liquid-to-solid phase transformation at the trailing edge of the weld nugget, and (c) cracks which may develop during the cooling of the weld area adjacent the trailing edge of the weld nugget. This is in contrast to prior art stress-wave emission, weld-monitoring, applications where stress waves are detected and measured in association with short-duration occurrences, e.g., the detection of a crack or the monitoring of a spot weld. In such events, however, there are no continuous overlapping stress-wave signals which might cloud a particular desired measurement. The present invention, therefore, permits stress-wave emission techniques to be used for the real-time monitoring of the weld nugget size and the occurrence of cracking in a continuous weld, thereby to provide the ability to determine the acceptability of a weld.

In applying stress-wave emission techniques to the monitoring of continuous welds, it was found that when a continuous melting process is taking place and a substantially uniform input energy is applied to the weld area, a stress-wave emission detector will detect relatively low-frequency stress waves containing a substantially uniform energy or RMS output level. The occurrence of an undesirable crack in the weld area, as the area cools adjacent the trailing edge of the weld nugget, causes the resultant stress-wave energy to contain higher frequencies as well as higher output levels. Similarly, if the input weld energy from a laser is insufficient for making an acceptable weld, the stress-wave energy emitted from the weld area will correspondingly be lower and thus a bad or a weak weld having an insufficient nugget volume can be detected.

Referring now to FIG. 1, a pair of articles 12 and 14 are positioned to be welded together along a seam 16 with a beam of radiation 18 from a laser 20. As the continuous weld is being formed along seam 16 by steadily moving both articles 12 and 14 at a predetermined distance and speed past a stationary laser 20, or vice versa, stress waves are continuously emitted from the weld area as a result of the solid-to-liquid phase transformation, the liquid-to-solid phase transformation, and cracks which may develop in the weld area. The stress-wave signals emitted from the weld area are detected by a piezoelectric differential transducer 22 (hereinafter referred to as sensor 22) which is preferably in continuous engagement with one of the two articles 12 and 14. Alternatively, sensor 22 can be mounted for non-contact detection purposes to a part of the laser welding apparatus (not shown), such as, for example, a base or a clamp, which both comprises material having a bulk sonic velocity which closely corresponds to the velocity of sound in the material of articles 12 and 14, and is in continuous contact with either one or both of articles 12 or 14 during the welding process.

The signals which are detected by sensor 22 comprise mechanical waves which are: (a) generated by other electrical or mechanical components in proximity to the system of FIG. 1, but not shown; (b) generated in articles 12 and 14 or sensor 22 due to non-transient factors such as temperature and strain variations; and (c) stress waves, comprising bulk and surface waves, propagating from the weld area in articles 12 and 14 while the articles are being welded.

During the welding process, energy is released from the weld area in the form of stress waves which, in turn, along with the possible unwanted mechanical waves generated by other electrical or mechanical components and in articles 12 and 14 or sensor 20 as indicated above, excite sensor 22. Depending on wave damping at the interfaces, the traveling mechanical stress impulses will cause sensor 22 to provide output voltage changes which are almost proportional to the amplitude of the impulses. Sensor 22, however, should preferably be chosen to have a natural frequency, which can be any frequency as, for example, 1 megahertz, which falls within the frequency range of the emitted stress waves from the weld area, but preferably outside the frequency range of the unwanted mechanical waves generated by other sources. In this manner, sensor 22 acts as a filter to generate an electrical output signal primarily representative of the stress waves emitted from the weld area and possibly including a very small component of the substantially attenuated unwanted mechanical waves from other sources. Because of the low amplitude of the stress-wave pulses, it is advantageous to provide for good transmission of the mechanical stress waves or amplification of the sensor's output voltage.

In an arrangement for monitoring a continuous weld, according to the present invention and as shown in FIG. 1, sensor 22 is connected to a low-noise preamplifier 24 by leads 26. Preamplifier 24 should be of a design having a sensitivity which is preferably in the range of 1–4$\mu$V, but can include a sensitivity beyond this range. In any case, preamplifier 24 should be sufficiently sensitive for the particular application.

The output from preamplifier 24 is transmitted over lead 28 to a band-pass filter 30 which has a pass-band that falls at least partially within the natural frequency of sensor 22, but which falls outside the range of noise frequencies generated by other components in proximity to the system. Filter 30, therefore, functions to pass only the amplified electrical signals from sensor 22 representative of the emitted stress waves from the weld area while simultaneously eliminating any amplified electrical signal from sensor 22 representative of the unwanted mechanical waves from other sources. Filter 30 is preferably a fifth order, or higher, high-pass filter which is commercially available. The output of filter 30 on lead 32 is further amplified by an amplifier 34. A resistor 36 is preferably added to lead 32, as shown, to match the input impedance of amplifier 34. Amplifier 34 is of a design which advantageously has a fast slewing rate, such as, for example, a commercially available model 715 operational amplifier. The output of amplifier 34, having thus far been processed to provide excellent signal-to-noise ratios, is transmitted over lead 38 to a commercially available RMS voltmeter 40, as, for example, a Hewlett-Packard Model 3403C voltmeter. The output from RMS voltmeter 40 is transmitted to an X–Y recorder 42 over lead 44 where it is desired to obtain a permanent record of the weld for possible use in the subsequent repair of a defective weld, as will be explained hereinafter. X–Y recorder 42 can be a commercially available recorder, as, for example, a Hewlett-Packard Model 7402A recorder.

The output of RMS voltmeter 40, as might typically be recorded on X–Y recorder 42, is shown in FIG. 2. There, for a certain amount of laser power or input energy, the detected stress-wave emission signals are advantageously found to contain an almost uniform energy or RMS output level, as indicated in sections A, C and E of the curve of FIG. 2. If, for some reason, a crack should develop in the cooling weld area, the resultant stress-wave emission energy will contain higher frequencies as well as higher output levels. The higher output levels are capable of being detected by RMS voltmeter 40, and the occurrence of a crack would, therefore, result in a relative abrupt rise in the RMS energy level as shown in part B of the curve of FIG. 2. A change in laser power or input energy will similarlry cause a less abrupt change to occur in the RMS output level, as shown in part D of the curve of FIG. 2 where a decrease in laser power or input energy is detected. The RMS output level, as shown in parts A, C, D and E of FIG. 2, can advantageously be correlated to the size of the moving weld nugget at any instance of time. Since the RMS output level provides an indication of whether sufficient input energy is being supplied by laser 20 to form a weld nugget having a volume sufficient to make an acceptable weld, the output signal from RMS voltmeter 40 can, therefore, be used with known feedback circuitry 46 to control the amount of input energy supplied by laser 20 above a predetermined minimal RMS output level. The approximate minimal RMS output level required to form an acceptable weld can, of course, be easily predetermined by experimentally forming similar welds while recording the RMS output levels, testing the welds to determine their acceptability as to strength, etc., and correlating the data obtained from the tests with the RMS levels. Such predetermined minimal RMS output level can be used as a minimal threshold level for comparison with the curve obtained with X-Y recorder 42 for each subsequent continuous weld of a similar type.

It is, of course, also possible to determine the location of a crack or a weak weld area by using the curve of FIG. 2, obtained with X-Y recorder 42, once the starting point of the weld and the rate of speed at which the weld was formed is known. For example, from the curve of FIG. 2, a crack was formed between times T1 and T2 which can be correlated into a specified distance from the starting point of the weld. Similarly a weak weld area was formed between times T3 and T4 by a decreased input energy level which can also be correlated to a distance from the starting point of the weld. Knowing the location of such defects advantageously permits subsequent corrective action to be taken where the defect is determined to result in an unacceptable weld.

The use of an RMS voltmeter 40 and X-Y recorder 42 provides a relatively inexpensive means for detecting the formation of most microcracks in the weld area and for accurately determining the input energy level during a continuous weld. It should, however, be recognized that an RMS voltmeter has a time constant which may cause it to not fully react to certain energy-limited or non-periodic, wave-packet signals as may be found in stress waves emitted during the instantaneous formation of some microcracks.

In an alternative arrangement of the present invention, as shown in FIG. 3, the system of FIG. 1 is essentially duplicated except for the substitution of a spectrum analyzer 50 for the RMS voltmeter 40 of FIG. 1. Spectrum analyzer 50 can comprise, for example, a spectrum analyzer available from the Federal Scientific Corporation of New York, N.Y. sold under the tradename FFT-Ubiquitous. The X-Y recorder 52, connected to the output of spectrum analyzer 50 by lead 51, can comprise a commercially available recorder as, for example, a Hewlett-Packard Model 7402A recorder. Recorder 52 is, of course, only required where a permanent record of a weld is required for possible subsequent repair of a defect in the weld.

Ideal curves obtained with X-Y recorder 52 of FIG. 3, for frequencies within the pass-band of filter 30, are shown in FIG. 4. As stated hereinbefore, in the continuous melting process, low-frequency stress-wave emission signals containing an almost uniform energy or RMS output level are detected. A typical frequency range for such signal, as might be obtained with spectrum analyzer 50, is shown by curve 54 in FIG. 4. Curve 54 is shown as extending to a certain voltage amplitude $V_s^2$ in the spectrum between the frequencies $f_0$ and $f_1$ within the passband of filter 30. As was stated hereinbefore, when a crack occurs during the cooling of the weld area, the crack generates stress-wave signals having large bandwidths and excessive energy levels. The occurrence of a crack might produce a frequency range as shown in the curve 56 of FIG. 4 as determined by spectrum analyzer 50 and recorded by X-Y recorder 52. Curve 56 is shown as having a slightly higher amplitude than that of curve 54 and extending between frequencies $f_0$ and $f_2$ within the passband of filter 30. The extended frequency range between frequencies $f_1$ and $f_2$ is a result of the frequencies generated in the stress waves emitted from the developing crack. It is, of course, also possible to detect certain input energy level changes by noting amplitude changes in the curve 54 of FIG. 4. However, as is known to those skilled in the art, a spectrum analyzer has certain limitations in the ability to accurately measure input energy level changes.

As explained above, it becomes evident that the system of FIG. 3 can be used to determine changes in the input energy level to a weld area and to accurately detect cracks forming in the cooling weld area. The ability of spectrum analyzer 50 to accurately check the frequency content of the emitted stress-wave signal permits the system of FIG. 3 to accurately determine if a microcrack has formed in the continuous weld area being monitored. The spectrum analyzer 50, however, does not provide as accurate a measurement of the input energy or RMS output level as might be found with the RMS voltmeter 40 of FIG. 1.

Although each of the systems of FIGS. 1 and 3 will monitor a continuous weld to provide indications of input energy level changes and the formation of cracks, another alternative arrangement of the present invention as shown in FIG. 5 provides a continuous weld monitoring system for accurately determining both changes in input energy levels and the formation of microcracks in the moving weld area. By effectively combining the elements of the individual systems of FIGS. 1 and 3, any slight deficiency which might exist in either one of the systems of FIGS. 1 and 3 is overcome.

In FIG. 5, the sensor 22, preamplifier 24, filter 30 and amplifier 34 employ the same circuitry and provide the same function as the corresponding elements in the arrangements of FIGS. 1 and 3. The output signal from amplifier 34, on lead 38, is supplied to the input of both RMS voltmeter 40 and spectrum analyzer 50. The output from RMS voltmeter 40 and spectrum analyzer 50 on leads 44 and 51, respectively, are supplied to respective X-Y recorders 42 and 52, and also to feedback control circuitry 46 when desired. As explained hereinbefore in the discussion of the system of FIG. 1, feedback control circuitry 46 can be employed where it is desired to control laser 20 for maintaining a substantially uniform input energy level or for corrective action to repair a defective weld area. The RMS voltmeter 40 of FIG. 5 primarily will function to accurately measure the RMS output energy of the detected stress-wave signals emitted from the weld area while still providing a secondary check for the development of a crack as explained hereinbefore. Spectrum analyzer 50 in the system of FIG. 5 functions mainly to accurately indicate the periodic harmonic content of the detected stress-wave signals. For such purpose, a less expensive spectrum analyzer than the analyzer suggested for the system of FIG. 3, such as, for example, a model 3L5 spectrum analyzer by Tektroniks Inc., will provide accurate data.

It is, of course, possible to include within feedback control circuit 46 of FIGS. 1, 3 and 5 any known comparison circuit which compares the measured RMS energy level, or frequency spectral content of the detected stress-wave signal, with a threshold value which was experimentally obtained from similar continuous weld samples for automatically determining whether the RMS energy level and/or frequency spectral content is within the range of an acceptable weld. In this manner the acceptability of a continuous weld can be automatically determined instead of an operator interpreting the curves of the X–Y recorders 42 and/or 52. For subsequent corrective action, however, the curves obtained with X–Y recorders 42 and/or 52 would be required, although it is also possible to utilize circuitry capable of automatic operation for such purpose.

It is to be understood that the above-described embodiments are simply illustrative of the principles of the invention. Various other modifications and changes may be made by those skilled in the art which will embody the principles of the invention and fall within the spirit and scope thereof.

What is claimed is:

1. A method for monitoring a continuously moving weld being formed by a welding apparatus along a path between a first and a second article, the method comprising the steps of:
   a. detecting stress waves continually being emitted from the moving continuous weld area and propagating in the materials of the first and second articles;
   b. amplifying and filtering said detected stress wave signals; and
   c. continuously measuring the RMS energy level of said amplified and filtered stress-wave signals for deriving both an accurate measurement of the input energy level applied to the continuouos weld area by the welding apparatus and an indication of the development of a microcrack in the continuous weld area from a momentary significant increase in said RMS energy level.

2. A method according to claim 1 comprising the additional step of:

concurrent with step (c)
   d. continuously measuring the frequency spectral content of said amplified and filtered stress-wave signals for providing an accurate indication of the development of a microcrack in the continuous weld area from a momentary significant increase in the frequency spectral content of the continuously measured signal.

3. A method according to claim 1 comprising the additional step of:
   d. generating a feedback signal to the welding apparatus in response to the detection of a significant momentary variation in said continuously measured RMS energy level for controlling the welding apparatus to provide a substantially constant input energy level to the continuous weld.

4. A method for monitoring a continuous weld being formed by a welding apparatus between a first and a second article, the method comprising the steps of:
   a. detecting stress waves continually being emitted from the moving continuous weld area and propagating in the materials of the first and second articles;
   b. amplifying and filtering said detected stress-wave signals; and
   c. continuously measuring the frequency spectral content of said amplified and filtered stress-wave signals for deriving both an accurate indication of the development of a microcrack in the continuous weld area from a significant momentary increase in the frequency spectral content of the continuously measured signal and an indication of the input energy level applied to the continuous weld area by the welding apparatus from the amplitude of said continuously measured signals.

5. Apparatus for monitoring a continuously moving weld being formed by a welding apparatus along a path between a first and a second article comprising:
   a. a sensor for detecting the stress waves continually propagating in the material of said articles during the formation of the weld to produce an electrical output representative of the detected waves;
   b. a first signal processing means comprising:
      i. an amplifier for amplifying the electrical output from said sensor; and
      ii. a band-pass filter connected to the output of said amplifier for generating an analog output signal within a pass-band falling outside the range of frequencies normally generated by components in proximity to the apparatus; and
   c. second signal-processing means connected to the output of said first signal-processing means comprising:
      i. means for continuously measuring the RMS energy level of said output signal from said first signal-processing means and deriving both an accurate indication of the input energy level applied to the continuous weld area by the welding apparatus and an indication of the development of a microcrack in the continuous weld area from a momentary significant increase in said continuously measured RMS energy level.

6. Apparatus according to claim 5 wherein said second signal-processing means further comprises:
   ii. means for continuously measuring the frequency spectral content of said output signal from said first signal-processing means for deriving an accurate indication of the development of at least a microcrack in the completed weld area from the detection of a momentary significant increase in the frequency spectral content in said continuously measured signal.

7. Apparatus according to claim 5 wherein said second signal-processing means further comprises:
   ii. means for detecting significant fluctuations in said continuously measured RMS energy level and generating a feedback signal to the welding apparatus in response to a detected significant fluctuation in said RMS energy level for controlling the welding apparatus to provide a substantially constant input energy level at the continuous weld area.

8. Apparatus according to claim 5 wherein said second signal-processing means further comprises:
   ii. means connected to the output of said RMS energy level measuring means for comparing the continuously measured RMS energy level with a predetermined threshold level for indicating an acceptable weld when said RMS energy level exceeds said threshold level.

9. Apparatus for monitoring a continuously moving weld being formed by a welding apparatus along a path between a first and a second article comprising:
 a. a sensor for detecting the stress waves continually propagating in the material of said articles during the formation of the weld to produce an electrical output representative of the detected waves;
 b. a first signal-processing means comprising:
  i. an amplifier for amplifying the electrical output from said sensor; and
  ii. a band-pass filter connected to the output of said amplifier for generating an analog output signal within a pass band falling outside the range of frequencies normally generated by components in proximity to the apparatus; and
 c. second signal-processing means connected to the output of said first signal-processing means comprising:
  i. means for measuring the frequency spectral content of said output signal from said first signal-processing means to derive both an accurate indication of the development of at least a microcrack in the cooling continuous weld area from the detection of a momentary significant increase in the frequency range within the measured signals, and an indication of the approximate input energy level applied to the continuous weld area by the welding apparatus from the amplitude level of said measured frequency spectrum signal.

10. Apparatus according to claim 9 wherein said second signal-processing means further comprises:
 ii. means for providing an indication of the time when significant variations occur in the amplitude and frequency content of the measured frequency spectral signals, said indications being capable of being compared with both the starting time and the starting location of the continuous weld for determining the location of a microcrack and a weak weld within said continuous weld area.

11. Apparatus according to claim 9 wherein said second signal-processing means further comprises:
 ii. means for detecting significant fluctuations in the amplitude of said continuously measured frequency spectrum signal and generating a feedback signal to the welding apparatus in response to a detected significant fluctuation of said signal amplitude for controlling the welding apparatus to provide a substantially constant input energy level at the continuous weld area.

12. Apparatus for monitoring a continuously moving weld being formed along a path between a first and a second article by a welding apparatus, the apparatus comprising:
 a. a sensor for detecting the stress waves continually propagating in the material of said articles during the formation of the weld to produce an electrical output representative of the detected waves;
 b. first signal-processing means comprising:
  i. an amplifier for amplifying the electrical output from said sensor; and
  ii. a band-pass filter connected to the output of said amplifier for generating an analog output signal within a pass band falling outside the range of frequencies normally generated by components in proximity to the apparatus; and
 c. second signal-processing means connected to the output of said first signal-processing means comprising:
  i. means for measuring the RMS energy level of the output signal from said first signal-processing means to provide an accurate indication of the input energy level delivered by the welding apparatus to the continuous weld area; and
  ii. means for concurrently measuring the frequency spectral content of the output signal from said first signal-processing means to provide an accurate indication of the development of a microcrack in the continuous weld area by the detection of a significant momentary increase in the spectral content of the measured frequency spectrum signal.

13. Apparatus according to claim 12 wherein said second signal-processing means further comprises:
 iii. means for providing an indication of the location of either one of a weak weld area and a microcrack within the continuous weld by providing an indication of the time when significant fluctuations occur in the amplitude of the measured RMS energy level and the frequency range of the measured frequency spectral, signal, respectively, with respect to both the starting time and the starting location of the continuous weld.

14. Apparatus according to claim 12 wherein said second signal-processing means further comprises:
 iii. means for detecting significant fluctuations in the amplitude of said measured RMS energy level and generating a feedback signal to the welding apparatus in response to a detected significant fluctuation for controlling the welding apparatus to provide a substantially constant input energy level at the continuous weld area.

* * * * *